(12) United States Patent
Huber et al.

(10) Patent No.: US 10,471,560 B2
(45) Date of Patent: Nov. 12, 2019

(54) MACHINING DEVICE FOR MACHINE-ASSISTED PRODUCTION AND MACHINING OF DENTAL WORKPIECES

(71) Applicants: Martin Huber, Pfarrwerfen (AT); Alfons Wörmer, Bischofshofen (AT)

(72) Inventors: Martin Huber, Pfarrwerfen (AT); Alfons Wörmer, Bischofshofen (AT)

(73) Assignee: DMU Dental Manufacturing Unit GmbH, Salzburg (AT)

( * ) Notice: Subject to any disclaimer, the term of this patent is extended or adjusted under 35 U.S.C. 154(b) by 447 days.

(21) Appl. No.: 15/113,070

(22) PCT Filed: Jan. 21, 2015

(86) PCT No.: PCT/EP2015/000100
§ 371 (c)(1),
(2) Date: Jul. 21, 2016

(87) PCT Pub. No.: WO2015/110259
PCT Pub. Date: Jul. 30, 2015

(65) Prior Publication Data
US 2016/0346888 A1   Dec. 1, 2016

(30) Foreign Application Priority Data
Jan. 20, 2014   (DE) .................. 10 2014 000 864.9

(51) Int. Cl.
*B23Q 3/157*    (2006.01)
*B23Q 7/10*     (2006.01)
(Continued)

(52) U.S. Cl.
CPC ............ *B23Q 7/10* (2013.01); *A61C 13/0004* (2013.01); *A61C 13/0022* (2013.01);
(Continued)

(58) Field of Classification Search
CPC ............... Y10T 483/16; Y10T 483/165; Y10T 483/1705; Y10T 483/1714;
(Continued)

(56) References Cited

U.S. PATENT DOCUMENTS 4,847,960 A * 7/1989 Hafla ...................... B23B 3/162
29/40
7,292,913 B2   11/2007 Tokutake et al.
(Continued)

FOREIGN PATENT DOCUMENTS

DE         8525630 U1    12/1985
DE         19521846 A1 * 12/1996
(Continued)

OTHER PUBLICATIONS

Machine Translation EP 1285725 A2, which EP '725 was published Feb. 2003.*
(Continued)

*Primary Examiner* — Erica E Cadugan
(74) *Attorney, Agent, or Firm* — Ann M. Knab; Thad McMurray

(57) ABSTRACT

The invention relates to a machining device for the machine-assisted production and machining of dental workpieces (16), particularly of artificial teeth and/or other dental replacement parts, the at least one workpiece (16) being clamped in at least one workpiece retainer (11) which can be raised, lowered and rotatably driven, is positioned on a rotational axis (9), and, for the purpose of machining, feeds said workpiece (16) to at least one tool spindle (4, 5, 6) that is rotationally driven and has a tool (7) secured thereto, an additional tool retainer (2, 2a, 2b) with a plurality of tools (7) arranged thereupon being associated with said workpiece retainer (11, 11a, 11b) and lying opposite on one side thereof, and a workpiece changer (22, 22a, 22b) which
(Continued)

receives the workpieces (16, 16a, 16b, 16c) to be machined, such that they can be exchanged, being arranged on the other side of said workpiece retainer (11, 11a, 11b).

9 Claims, 16 Drawing Sheets

(51) Int. Cl.

| | | |
|---|---|---|
| | *B23Q 7/04* | (2006.01) |
| | *B23Q 39/02* | (2006.01) |
| | *B23B 11/00* | (2006.01) |
| | *A61C 13/00* | (2006.01) |
| | *B23Q 11/08* | (2006.01) |
| | *B23Q 39/04* | (2006.01) |
| | *B23Q 1/62* | (2006.01) |
| | *B23B 3/06* | (2006.01) |
| | *B25J 11/00* | (2006.01) |
| | *B23Q 3/155* | (2006.01) |

(52) U.S. Cl.
CPC .............. *B23B 3/065* (2013.01); *B23Q 1/623* (2013.01); *B23Q 3/15706* (2013.01); *B23Q 3/15713* (2013.01); *B23Q 3/15766* (2013.01); *B23Q 7/046* (2013.01); *B23Q 7/047* (2013.01); *B23Q 11/0891* (2013.01); *B23Q 39/024* (2013.01); *B23Q 39/042* (2013.01); *B25J 11/005* (2013.01); *B23Q 3/15722* (2016.11); *B23Q 2003/15537* (2016.11); *B23Q 2003/155418* (2016.11); *B23Q 2003/155428* (2016.11); *B23Q 2003/155446* (2016.11); *Y10S 483/902* (2013.01); *Y10T 29/519* (2015.01); *Y10T 29/5114* (2015.01); *Y10T 483/115* (2015.01); *Y10T 483/16* (2015.01); *Y10T 483/1705* (2015.01); *Y10T 483/1714* (2015.01); *Y10T 483/1724* (2015.01); *Y10T 483/1755* (2015.01); *Y10T 483/1788* (2015.01); *Y10T 483/1882* (2015.01)

(58) Field of Classification Search
CPC ............ Y10T 483/1724; B23Q 39/024; B23Q 7/04–7/048; B23Q 3/155–3/15793

USPC ......... 483/14, 15, 18, 22, 26; 29/27 R–27 C, 29/563–38.9
See application file for complete search history.

(56) References Cited

U.S. PATENT DOCUMENTS

| | | | |
|---|---|---|---|
| 8,376,921 B2 | 2/2013 | Wember | |
| 9,242,327 B2 | 1/2016 | Evertz et al. | |
| 2003/0050160 A1* | 3/2003 | Popp | ..................... B23Q 1/015 483/14 |
| 2006/0008774 A1 | 1/2006 | Orth et al. | |
| 2009/0191017 A1 | 7/2009 | Wember | |
| 2009/0290948 A1 | 11/2009 | Basler | |
| 2011/0137452 A1 | 6/2011 | Boyes et al. | |
| 2011/0280692 A1 | 11/2011 | Evertz et al. | |
| 2013/0203572 A1 | 8/2013 | Denkmeier et al. | |
| 2013/0216323 A1 | 8/2013 | Reck et al. | |

FOREIGN PATENT DOCUMENTS

| | | | |
|---|---|---|---|
| EP | 1285725 A2 * | 2/2003 | |
| EP | 1927430 A2 | 6/2008 | |
| GB | 2271945 A * | 5/1994 | |
| JP | H08152911 A | 6/1996 | |
| JP | 10-314187 A * | 12/1998 | |
| JP | 2003-334787 A * | 11/2003 | |
| RU | 2170069 C2 | 7/2001 | |
| SU | 1736468 A1 | 5/1992 | |
| WO | WO-2018141728 A1 * | 8/2018 | |

OTHER PUBLICATIONS

Merriam-Webster's Collegiate Dictionary, 10th ed., p. 1013, dictionary definition of "robot", copyright 1998.*
Machine Translation, DE 19521846 A1, which DE '846 was published Dec. 1996.*
Machine Translation of JP 10-314187, which JP '187 was published Dec. 1998.*
Machine Translation of JP 2003-334787, which JP '787 was published Nov. 2003.*

* cited by examiner

MACHINING DEVICE FOR MACHINE-ASSISTED PRODUCTION AND MACHINING OF DENTAL WORKPIECES

CROSS-REFERENCE TO RELATED APPLICATIONS

This application is a National Stage application of International patent application PCT/EP2015/000100 filed on Jan. 21, 2015, which claims priority to German patent application No. 102014000864.9 filed on Jan. 23, 2014, the disclosures of which are incorporated herein by reference in their entirety.

The invention relates to a machining device for dental applications.

Machining devices of this kind are characterized in that one or several artificial teeth can be produced in the rooms of the dental practice supervised by the dentist—even in presence of the patient. Accordingly, no industrial production and machining of one or more artificial teeth using industrial machines takes place in the dental laboratory, but instead highly accurate production and machining of one or more artificial teeth using a machining device which is as small as possible and easy to handle.

The invention is based on a machining device as has been produced by developments of the company Sirona Dental Systems GmbH according to EP 1 614 396 B1. Initially, a three-dimensional image of the dental replacement part is produced and subsequently the dental replacement part is produced based on the CAD/CAM principle in a machining device from a raw material by a chip-removing machining process. Only driven tools without tool magazine are available. Thus, this provides the disadvantage of a required retooling of the tools as after the application of a first set of machining tools the machine needs to be stopped and a second set of machining tools needs to be clamped. In particular, different blank materials require different sets of tools. Furthermore, only one workpiece blank can be processed at a time.

A second machining device of the same patent owner has become known in which a workpiece retainer which can be raised, lowered and rotated is provided in which the workpiece blank is clamped for the purpose of machining.

To the left and to the right of the workpiece retainer which carries the tooth to be machined spindles which can be fed and moved away are provided which are mounted in tool axes which are offset to one another and which can be fed to the workpiece retainer for the purpose of machining the artificial tooth.

However, this known device has the disadvantage that only one single tooth to be machined is received in the workpiece retainer. Thus, it is required to perform the entire machining program for the production of the tooth before—after the end of the entire machining process—the fully-machined tooth can be removed from the workpiece retainer and replaced with a new tooth to be machined.

This creates the disadvantage that a time-consuming production of an individual tooth is required as the tooth always has to be machined to completion before a further tooth can be machined.

Changing the workpiece, that is to say unloading the fully-machined tooth and replacing it with a new workpiece to be machined, takes place manually. This also limits the way the device works as manual intervention is always necessary during the machining process, and during this time further machining cannot take place.

The arrangement is relatively large as the machining spindles with their drive elements are fed sideways and opposite to the central workpiece retainer, which results in a relatively large construction length of the machining device.

A further disadvantage is that the machining tools with the drive elements are fed to the workpiece retainer from both sides, which is associated with additional efforts to form the drive elements and which requires a more complex control as the control has to differentiate between the right and the left feed side of the machining device and has to be programmed.

The known concept is based on the fact that several tools can be coupled to a drive spindle, however, in case of the known concept, this leads to the disadvantage that both on the left and on the right side of the machining device a drive spindle has to be provided respectively, and that on every side the associated tool changers need to be arranged. This also requires large machine expenditure and involves high costs for the production of a machining device of this kind.

Therefore, the invention is based on the task of developing a machining device of the type mentioned at the beginning further in such a way that it can be produced with a substantially simpler design and a simplified control program at lower production costs.

In order to solve the set task the invention is characterized by the technical teaching of the claims.

The basic principle of the invention is based on the fact that the workpiece received in a multi-axis workpiece retainer is fed to a tool retainer which is disposed in another plane, said tool retainer carrying at least one rotatably driven spindle which remains on the plane which has been allocated to it, and that the workpiece to be machined which is clamped in the workpiece retainer is fed to this spindle with a tool which is disposed thereat exchangeably and machined thereat.

A feature of a first embodiment of the invention according to independent claim 1 is that the workpiece retainer is configured as a multi-axis robot on one side of which at least one tool retainer with a rotatably driven and exchangeable tool is arranged and that on the other side of the multi-axis workpiece retainer a tool changer which is configured as a tool storage is arranged in which the workpieces to be machined are received exchangeably.

A feature of this embodiment is that according to this inventive idea the tool retainer gets by with only one single rotatably driven spindle in the minimum case to which a plurality of tools can be coupled. In order to machine a workpiece the workpiece clamped in the multi-axis workpiece retainer is fed to this spindle and machined by the tool clamped in the spindle.

In this way, the effort to produce a tool retainer is minimized considerably, as in the simplest case only one single rotatably driven spindle with a plurality of tools which can be secured thereto is provided and the spindle does not perform any movements in space as the machining movements by the workpiece retainer holding the workpiece are performed at the spindle. Moving spindles are subject to the gyroscopic effect and thus to acting forces. These forces are passed on to the mechanical system of the machining unit and this can have a negative influence on the stability of the machining process. A spindle which is connected to the base frame of the machining unit rigidly is not exposed to these effects.

Needless to say, the invention is not limited to the arrangement of one single rotatably driven spindle on the tool retainer. In another embodiment it can be provided that several rotatably driven spindles with tools arranged thereon are arranged, wherein, however, in the preferred case of application only one tool retainer with a rotatably driven spindle arranged thereat is arranged.

In this case, the workpiece retainer is preferably configured as a multi-axis robot, and in a particularly preferable embodiment at least as a 5-axis robot which is thus capable of acting in at least 5 different machining axes. It comprises a machining head which is suitable for clamping a workpiece intended for machining. However, it is important that it comprises one or more handling devices apart from the clamping head for a workpiece to be machined, which are suitable for removing a required tool from a tool storage and feeding the tool to the tool retainer in order to attach this new tool to the rotatably driven spindle or to couple it in any other manner non-rotatably.

At the same time, the workpiece retainer can be provided with a further mounting for the (old) tool to be removed from the spindle.

Then, a tool change is performed as follows:

At first, the workpiece retainer with its handling device advances to the bottom and picks up the old tool which is still received within the spindle.

The additional handling device which is disposed on the opposite side of the workpiece retainer removes a new tool from the tool storage. Subsequently, the machining device is turned by 180° in order to return the old tool which has been removed from the spindle previously to the tool storage and at the same time to feed the new tool which is now hanging from the bottom of the machining device to the spindle located at the bottom.

Arranging two handling devices, which are positioned opposite to one another, at the multi-axis machining device, wherein every handling device is preferably configured as a fork, offers the advantage that a particularly easy tool change is possible.

The respective fork is equipped with a plug-in recess which is suitable for removing a first tool from the tool storage, and the other handling device which is also configured as a fork is suitable for also receiving the old tool included in the plug-in device of the rotatably driven spindle in the plug-in recess of the fork.

Due to the fact that the workpiece retainer may be rotated by 180°, one fork is always arranged at the top and one fork at the bottom, and it is possible to always transport and handle two different tools by arranging them in the top and bottom fork, respectively.

Instead of using fork-like handling devices for holding a set of tools, it is also possible to use other suitable handling devices.

Due to the fact that the tool changer is arranged at the multi-axis workpiece retainer at the same time—a machining device that is particularly small and space-saving may be created in very small spaces in this manner.

In a particular embodiment of the invention it is provided that the entire machining device is configured as a table device such that it is possible to machine dental machining pieces, such as plastic or ceramic teeth, etc., in a very small space.

In a first embodiment of the invention it is provided that the workpiece storage is configured as a rotary table and is formed at a vertical distance above the blank workpieces to be machined that are carried by the workpiece changer.

In this case, below the workpiece changer that is also configured as a rotary table, a 5-axis workpiece retainer is located, at which the tool changer is arranged, as has been described previously.

In this case, vertically below the workpiece retainer the tool retainer with the at least one rotatably driven spindle is arranged to rotatably drive the only tool.

Provided that only one single spindle is used—that is to be equipped with a plurality of tools—the arrangement of such a spindle on a rotary table may be dispensed with. Then, it is sufficient to fixedly arrange the spindle at a base plate of the machining device.

In a further development of the invention, however, it may also be provided that several spindles are arranged on a common rotary table in a manner evenly distributed around the circumference, wherein it is possible to assign a different tool to every spindle.

The arrangement of several spindles with various tools offers the advantage that the workpiece retainer may perform a number of different machining processes at various tools without the need for a tool change.

The invention is not limited to the arrangement of the tool storage vertically above the workpiece-carrying workpiece changer.

In a further embodiment it may also be provided that the tool storage is arranged on a different plane of the machining device, for example below the workpiece changer and above the workpiece retainer or also below the workpiece retainer and above the rotary table on which the one or more rotatably driven spindles are arranged.

However, it is preferred that the tool storage is arranged above the workpiece changer in a manner so as to be vertically raisable and lowerable, and also that the workpiece changer is configured so as to be rotatable and vertically adjustable. In this way, these two devices (tool storage and workpiece changer) may be fed to the 5-axis-workpiece retainer and removed therefrom, thus accelerating the tool change and the change of the workpiece.

In a third embodiment of the invention it may be provided that instead of the proposed rotary table for the workpiece changer and the tool storage, linear displacement drives are used now. Instead of the rotational movements, in this third embodiment the tools are supplied to the workpiece retainer on a linear slide that can particularly easily remove the workpieces from the workpiece storage with its handling device as this slide is configured as a displaceable slide.

The same applies to the workpiece changer on which the workpieces to be machined are arranged, and which, in this preferred configuration, is also configured as a slide that may be moved in the linear direction—preferable in the horizontal direction.

Here, too, particularly simple feed movements to the multi-axis workpiece retainer arise.

In the same manner, it may be provided with this exemplary embodiment that instead of a lower rotary table as a tool retainer, now a slide is provided that is also driven in a way so as to be displaceable in the horizontal direction, said slide also accommodating one or more rotatably driven spindles with tools respectively arranged thereon.

Instead of the rotational arrangement (in the manner of rotary tables) of tool storage, workpiece changer and tool retainer, the above-mentioned elements may be replaced with linearly displaceable slide arrangements, accordingly.

However, it is important with all embodiments that the tool changer is connected with the multi-axis workpiece retainer and forms one part therewith, in order to thus achieve a particularly compact structure.

As has been described previously, it applies to all embodiments that the workpiece clamped into the workpiece retainer is now fed to the one or more rotatably driven spindles by means of the multi-axis workpiece retainer, because the tools required for the chip-removing machining of the workpiece are arranged on the spindles, respectively.

As with the first rotatory exemplary embodiment (rotary table) it may also be provided in this third embodiment that only one single rotatably driven spindle is provided that is fixedly arranged at a base plate of the machining device, wherein it is, however, possible to equip the spindle with a plurality of various tools subsequently.

Also, there are—in a fourth embodiment—hybrid forms between the rotational members, as described in the first exemplary embodiment, and linearly displaceable members, as described in the third exemplary embodiment.

With this hybrid form it is provided for example that the linearly displaceable slides of workpiece changer and tool storage are not displaceable in the horizontal direction but in the vertical direction.

Thus, simple slides may be provided that are displaceable in the Y-direction. However, it is also possible—in all embodiments—to configure the slides as X-Y slides.

In any case, the workpiece retainer that carries the workpiece to be machined, must be capable of managing at least three axes (X, Y and Z axis) and of performing the rotational and swiveling movements associated therewith, resulting in an at least 5-axis-workpiece retainer.

The inventive machining device is built in a particularly compact manner and has small weight, so that it can readily be arranged as a table device in a dental practice. If the described functional parts, that is to say tool storage, workpiece changer and tool retainer, are arranged so as to lie on top of each other vertically, they can be covered by suitable cover hoods so that only the approximately central machining plane of the device is visible anymore. Said central machining plane is formed by the workpiece retainer arranged in the area of the central plane and at least one rotary spindle associated therewith.

It has been explained previously that the tools are arranged on a rotary table and that said rotary table is arranged vertically above a workpiece changer that is also configured as a rotary table, on which the blanks (workpieces) to be machined are arranged.

First Embodiment

The present invention describes a preferred embodiment in which the workpiece changer and the tool storage are arranged in the upper area of the machining device in an interlocking manner for the purpose of space saving (in the vertical direction). For this purpose, the rotary table function is replaced by a plurality of arms that are evenly arranged around the circumference, each arm being directed approximately horizontally and carrying the tools that are directed vertically downward at the free outer end thereof on an inner circle.

Radially to the outside of said circle, further arms are arranged on a further circumferential circle which arms are also directed in the horizontal direction and overlap the first-mentioned arms of the workpiece storage and carry plug-in devices at the front free ends thereof into which the workpieces to be machined are inserted.

The arms of the upper plane that are assigned to the workpiece storage, are rotatably driven commonly and are separate from the arms of the tool storage that is arranged in the lower plane and that is also driven rotatably.

Therefore, instead of rotary tables, arms directed radially to the outside are used in two planes which are arranged on top of each other and nested into one another, each arm comprising a suitable plug-in device for receiving either a workpiece or a tool at the radial outer end thereof.

The upper plane of the arms (that are assigned to the tool storage for example) is driven rotatably, separately from the lower plane of the workpiece changer that is arranged below. Thereby, a particularly simple, vertically superimposed and compact structure of tool storage and workpiece changer is produced, which has not been known so far.

Second Embodiment

A feature of the second embodiment of the invention is that based on a central workpiece retainer which is rotatably driven on several axes and in which the workpiece to be machined is clamped and arranged movably, a tool retainer with a plurality of tools arranged thereon is provided oppositely on the one side, and opposite the tool retainer a workpiece changer is arranged in which the workpieces to be machined are received exchangeably.

The given technical teaching offers the advantage of a simplified construction, as now a machining device can be used to automatically machine a plurality of workpieces (teeth) without the need of manual intervention during the machining process.

The central concept of the invention is based on a central, preferably vertical, axis around which two carousels turn independently of one another. This enables manual and/or machine-based loading of the machine with blanks during the milling and grinding process and thus increases the efficiency of the machine. The workpiece changer ensures that the operator has to interact less with the machine and thus the efficiency of the machine is increased.

This means that in a preferable embodiment the workpiece to be machined is received in a workpiece retainer such that it can be rotated, lowered and swiveled and such that it can be moved in this connection such that the workpiece clamped thereat can be fed towards a rotary table configured as a carousel on which a number of rotatably driven tools are arranged.

Here, it is preferable if the rotatably driven tools on the rotary table are driven by at least one tool spindle. This means that, only in the easiest case, only one single rotatably driven tool spindle has to be available, and that the tool spindle can be coupled to a number of tools arranged on the rotary table.

This results in a particularly easy and space-saving construction as, in the easiest case, only one single rotatably driven tool spindle has to be arranged at the rotary table, while in the prior art at least two such rotatably driven tool spindles needed to be provided.

However, in a preferred embodiment of the invention it is also provided that several rotatably driven tool spindles are allocated to the tools, which is, however, not associated with an increased installation space, as it is indifferent with regard to the vertical installation space if one single tool spindle is arranged or several tool spindles.

If several tool spindles are provided, there is no longer the need for a number of coupling processes in order to couple a tool spindle each with a tool.

In order to provide for the most efficient machining of the workpiece it is preferable if the workpiece retainer, at which the workpiece to be machined is clamped, is configured as an X-Y-Z slide. In this way, it is ensured that the clamped workpiece can be rotated, swiveled and drawn in all three spatial directions in any spatial axis and coordinate with a desired degree of freedom.

Instead of using X-Y-Z slides other controllable devices which are freely movable in space can be used, such as for instance one respective rotatably driven threaded spindle arranged in the spatial coordinates X, Y and Z or general actuators which are changeably driven in all three spatial directions X, Y, Z. Actuators of this type can also be part of a multi-axis robot which is configured as a 6-axis robot, for instance. Instead of a multi-axis robot a scalar robot can also be used.

Thus, the invention is not limited to the arrangement of slide elements to hold the workpiece to be machined.

A substantial feature of the invention is that a workpiece changer is arranged opposite from the workpiece retainer, in which workpiece changer a number of workpieces to be machined are held detachably. Accordingly, it is a workpiece magazine in which the workpieces to be machined are either inserted after the machining process or removed from the magazine as blank parts in order to be clamped in the workpiece retainer and to be machined subsequently.

In a preferred embodiment of the invention the workpiece changer is configured as a rotary table at whose free rotatable part the blank workpieces are arranged one after another. Likewise, the fully-machined workpieces can be inserted in other machining or plug-in positions.

However, here, it is not necessary for the solution that the workpiece changer is configured as a rotary table.

In another embodiment it can be provided that the blank workpieces to be supplied are held in a magazine arranged one after another or one next to another and removed from this magazine.

Instead of a rotary drive for the workpiece changer, linear drives can be provided accordingly for supplying blank workpieces and for removing the machined workpieces.

The given technical teaching offers the advantage that a machining device according to the invention runs automatically in order to machine a plurality of teeth and does not require any manual intervention.

A machining process using the second embodiment is now performed as follows:

In a first machining step the workpiece retainer takes out a blank workpiece from the workpiece changer from any plug-in location, clamps it and advances into the machining position in the direction of the tool retainer arranged at the bottom which is preferably configured as a rotary table.

Then, a number of machining processes follow which all take place above the tool retainer and the tools which are rotatably driven thereat.

After the machining process has been completed, the workpiece retainer advances to the top in the direction of the workpiece changer with the fully-machined workpiece which is still clamped in, inserts the fully-machined workpiece into a free plug-in location, and picks up a blank workpiece from another plug-in location, which is clamped in, in turn, and supplied to the lower tool retainer for a new machining process.

In this way a plurality of workpieces (teeth) can be machined to completion, wherein a number of 5 to 15 workpieces is preferred. For instance, as a result, a full mouth reconstruction of an existing set of teeth with artificial teeth can be performed, wherein all of the teeth are machined consecutively, and manual intervention is not necessary any longer.

The invention offers the particular advantage of the small installation height and the low production costs as the rotary drive of the tool retainer only requires a conventional rotary motor and as one or several tool spindles are arranged at the tool retainer. Thus, such a device is ideally suited for being set-up in a dental practice because of its small outer dimensions, in association with a time-saving production of artificial teeth.

It is particularly space-saving if the workpiece retainer is configured as an X-Y-Z slide which is configured so that it can be raised and lowered in a vertical axis, and accordingly so that it can be supplied to and moved away from the tool retainer in the one direction and the workpiece changer in the opposite direction.

It also results in low space requirements if the workpiece changer is also configured as a rotary table as a small rotary drive is used here and no further measures are required anymore.

The invention is not limited to the rotary table configuration of the workpiece retainer and the workpiece changer as well as the X-Y-Z slide for the workpiece retainer.

In another embodiment of the invention it can be provided that one or more of the above-mentioned three elements (tool retainer, workpiece retainer, workpiece changer) are configured as linearly driven structural elements. This means that instead of being driven by a rotary drive, one or more of the above-mentioned elements can also be driven linearly.

Likewise, an additional rotary drive can be superimposed on the linear drive.

Furthermore, the invention is not limited to the workpiece retainer being configured as a X-Y-Z slide.

In another embodiment it can also be configured as a rotary table at the outer circumference of which the several workpieces to be machined are arranged.

This offers the advantage that several workpieces can be machined in one process step as in the workpiece retainer a number of workpieces are arranged which can possibly be machined at the same time.

The term "workpiece" is broadly defined in the present invention. The invention does not only relate to the production of artificial teeth but also of other dental parts from the dental sector. They include, for instance, abutment parts of implants or gingiva formers or the like. This means that not only is plastic machining of artificial teeth provided but also metal machining of the above-mentioned other parts.

For this reason the machining device according to the invention is suited for machining all parts for dental applications.

The subject matter of the present invention does not only result from the subject matter of the individual patent claims but also from the combination of the individual patent claims with each other.

All of the particulars and features disclosed in the documents, including the abstract, in particular the spatial configuration illustrated in the drawings, are claimed to be essential for the invention as far as they are novel over the prior art individually or in combination with one another.

Below, the invention is further explained on the basis of drawings which illustrate only on way of embodying the invention. In this connection, further features and advantages of the invention essential for the invention develop from the drawings and their description, in which.

Figure 1:
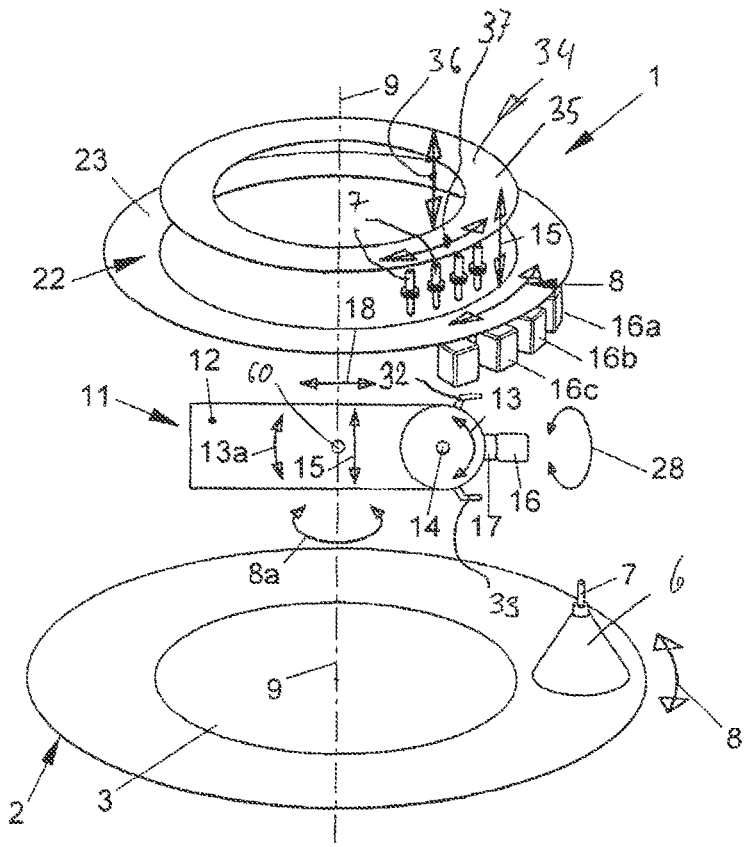
FIG. 1 shows a perspective view of a first embodiment

In the following description of the Figures the same reference numerals are used for the same parts. When a part with a particular reference numeral has been described sufficiently, this description will also hold true for all of the other parts with the same reference numeral mentioned hereinafter. Accordingly, it is renounced to always provide the same description for parts with the same reference numerals.

Figure 2:
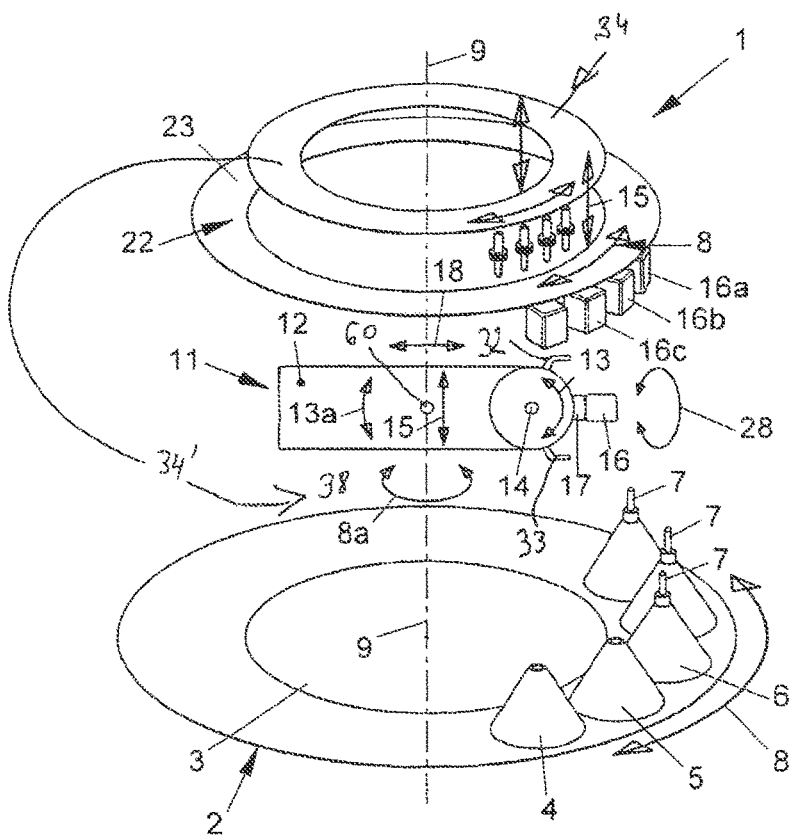
FIG. 2 shows a perspective view of a second embodiment deviating from the first embodiment

The machining device 1 of FIGS. 1 and 2 essentially consists of a lower rotary table 3 which is configured as a tool retainer 2 and on which in a first preferred exemplary embodiment only one single rotatably driven tool spindle 6 is arranged, the rotary drive of which is not illustrated in more detail.

The tool spindle 6 comprises a suitable coupling device, e.g. a plug-in coupling, into which a tool 7 is inserted and coupled. In the vertical plane above the tool retainer 2 the inventive workpiece retainer 11 is arranged which is preferably configured as a 5-axis manipulator or a 5-axis robot. It consists of a base body 12 and can perform a rotary movement in the arrow direction 8a and a linear displacement in the arrow directions 15 in the indicated arrow directions (direction of tilt 13a, displacement direction in arrow direction 18 in the X-axis).

Additionally, it carries a machining head which can be swiveled in the swivel axis 14 in the indicated direction of tilt 13. A workpiece holder 17 is disposed at the machining head, which workpiece holder is configured preferably as a plug-in recess into which a workpiece 16 to be machined can be inserted.

Thus, for the purpose of machining the workpiece 16 is coupled non-rotatably in the workpiece holder 17, and the rotary drive for moving the workpiece 16 can take place in the arrow directions 28, for instance.

Preferably, a handling device is arranged at the workpiece retainer 11, said handling device consisting of two forks 32, 33 arranged on top of each other, wherein the forks comprise suitable plug-in devices to remove a tool 7 from a tool storage 34 arranged above and to plug it onto the plug-in recess of the tool spindle 6.

On the other hand, for instance by using the lower fork 33, the tool 7 which is not used anymore can be removed from the tool spindle 6 and returned to the tool storage 34.

In a preferred embodiment, the tool storage 34 is configured such that it can be raised and lowered in the arrow direction 36 and is driven rotatably around the axis of rotation 9 in the arrow direction 37.

In the plane below the tool storage 34 a further rotary table 23 is arranged which is allocated to a workpiece changer 22.

At the workpiece changer 22 a plurality of workpieces 16a, 16b, 16c to be machined are arranged in a way evenly distributed around the circumference.

This rotary table 22 is also preferably driven rotatably in the arrow direction 8.

A workpiece 16 to be machined is simply removed by the workpiece retainer 11, with its front machining head and the workpiece holder arranged thereat, advancing to the top in the direction of the workpiece changer 22, coupling or clamping a blank workpiece thereat and by the workpiece retainer 11 returning to its basic position.

In order to machine a workpiece 16 which is clamped in the workpiece holder 17 of the workpiece retainer 11 the workpiece retainer 11 is advanced to the bottom in the arrow direction 15 along the axis of rotation 9 and the workpiece to be machined is supplied to the area of the tool 7, which is clamped in the tool spindle 6 and driven rotatably, by means of the multi-axis displacement of the workpiece retainer 11, where it is subjected to a number of machining steps.

Contrary to FIG. 1, FIG. 2 shows that it is not necessary for the solution to arrange the tool storage 34 in the uppermost plane. An arrow 34' indicates that the tool storage 34 can also be arranged at position 38, namely in the plane above the tool retainer 2.

The exemplary embodiment of FIG. 2 also shows that it is possible to arrange a plurality of rotatably driven tool spindles 4, 5, 6 on a common rotary table 3 instead of one single tool spindle 6 according to FIG. 1—which can actually be driven without a rotary table 3—such that the workpiece 16 clamped in the workpiece retainer 11 can be supplied to a plurality of tool spindles 4, 5, 6 equipped with different tools successively at a short interval.

As previously explained, according to the exemplary embodiment of FIG. 1 the rotary table 3 can be omitted accordingly, while it is available according to the exemplary embodiment of FIG. 2 and can be driven rotatably in the arrow direction 8.

Figure 3:
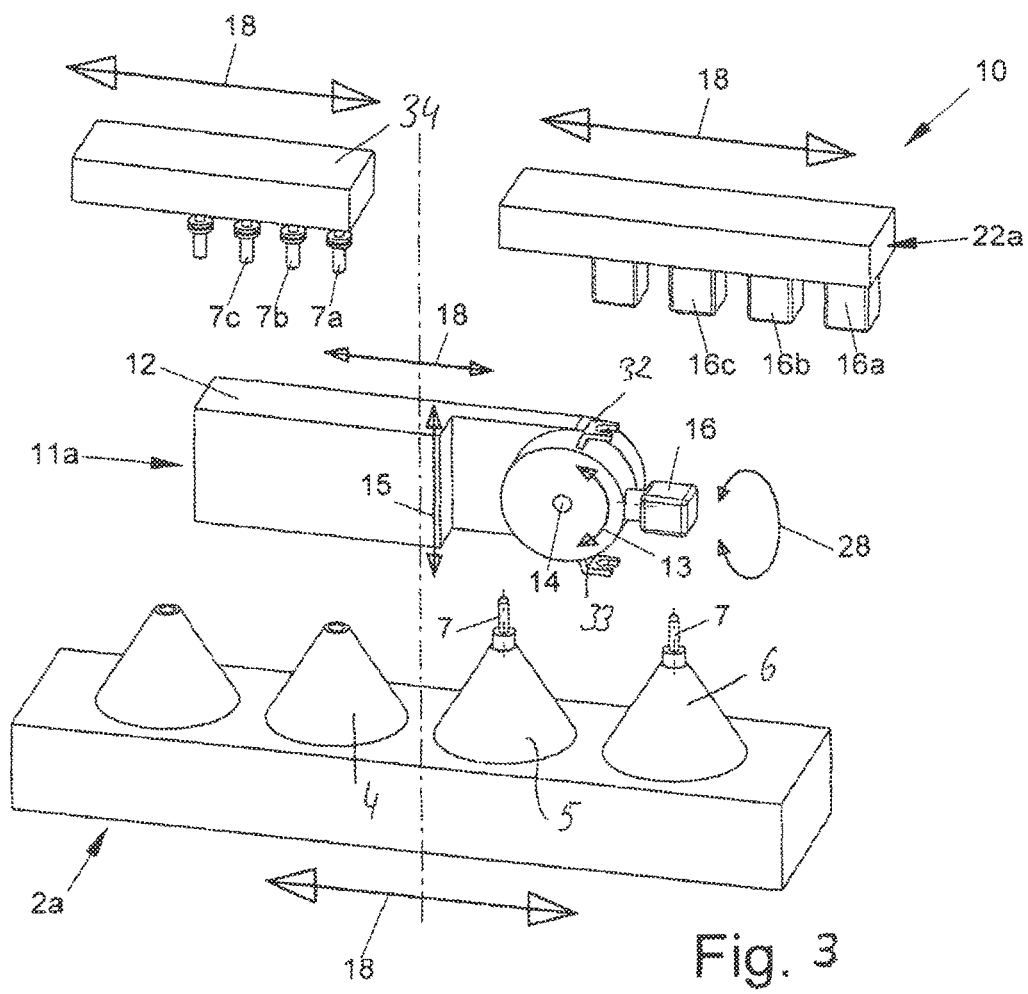
FIG. 3 shows a perspective view of a third embodiment with linearly driven slides

FIG. 3 shows that all of the rotatably driven parts according to FIGS. 1 and 2 can also be replaced by slides which can be moved linearly. The same reference numerals apply to the same parts. Here, it is apparent that the tool storage can now be configured as a slide which can be driven linearly in the arrow direction 18 and at the bottom side of which the tools 7, 7a, 7b, 7c are arranged.

Accordingly, a fundamentally different machining device 10 is described compared to the machining device 1 as the machining device 1 according to the FIGS. 1 and 2 works with rotatably moved parts while the exemplary embodiment of the machining device 10 according to FIG. 3 works with modules which can be moved translationally.

Figure 4:
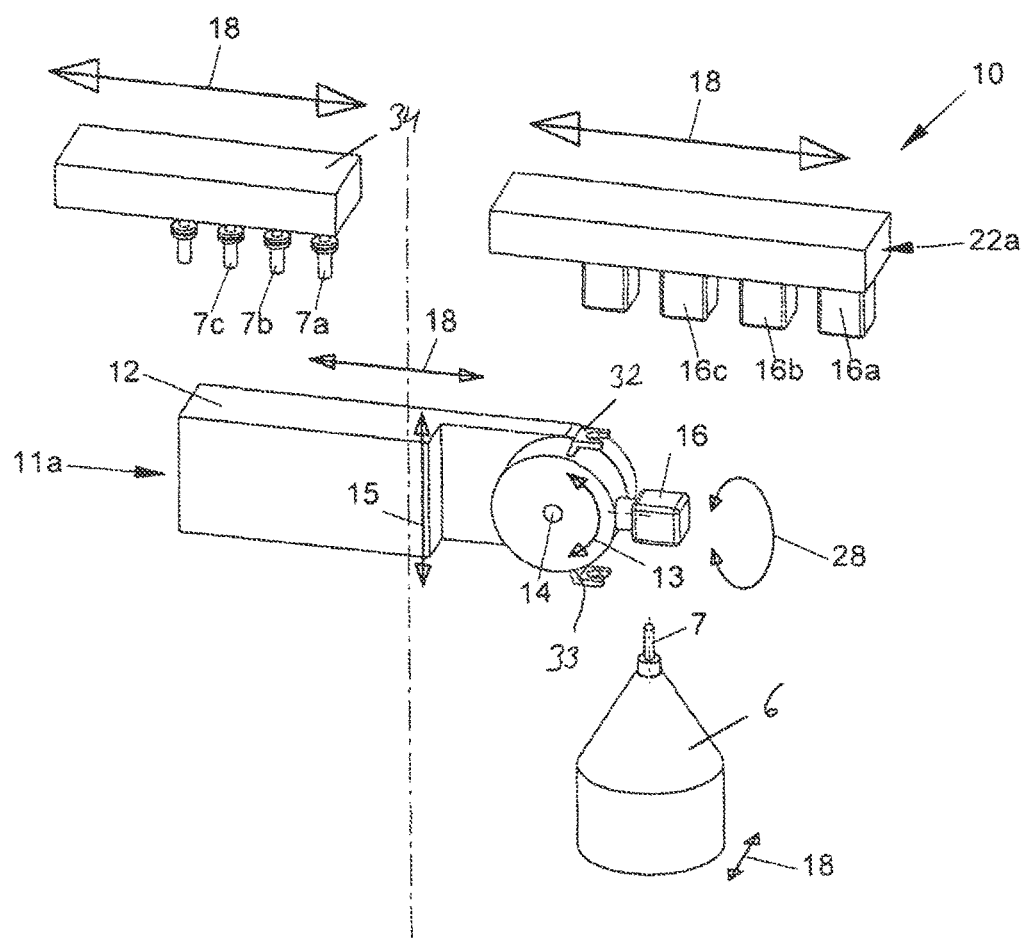
FIG. 4 shows an embodiment modified with respect to FIG. 3

Instead of the arrangement of several rotatably driven tool spindles 4 to 6 which can carry a different tool 7 each it is provided in FIG. 4 that only one single rotatably driven tool spindle 6 with one exchangeable tool 7 arranged therein is provided. Accordingly, the translationally movable slides according to FIG. 3 can be omitted.

In both embodiments according to FIGS. 3 and 4 it is apparent easily that the handling devices for changing the tools are configured as plug-in forks 32, 33 which enables a particularly fast and easy tool change of the tools 7 from the tool storage 34 in the direction of the tool spindle 4 to 6.

Figure 5:
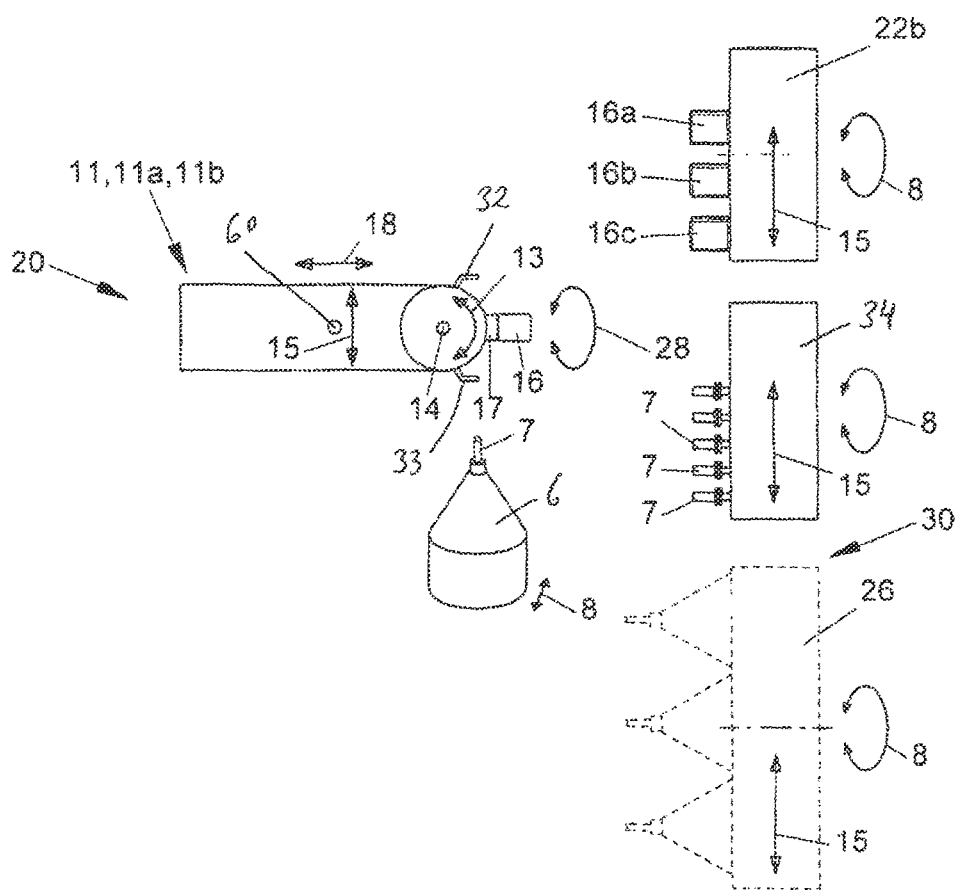
FIG. 5 shows a further embodiment modified with respect to FIG. 3

FIG. 5 shows a further development of the configuration according to FIG. 4 and it is apparent that the translationally movable slide according to FIG. 3 which carries the plurality of tool spindles 4 to 6 can also be arranged vertically, and that the different modules are arranged vertically aligned one below the other.

Only for the sake of completeness it is illustrated that the machining device 20 configured in this manner also works with a workpiece retainer 11, 11*a*, 11*b* and that the workpiece retainer is mounted in a rotary and swivel axis 60 such that it can be rotated and swiveled.

Figure 6:
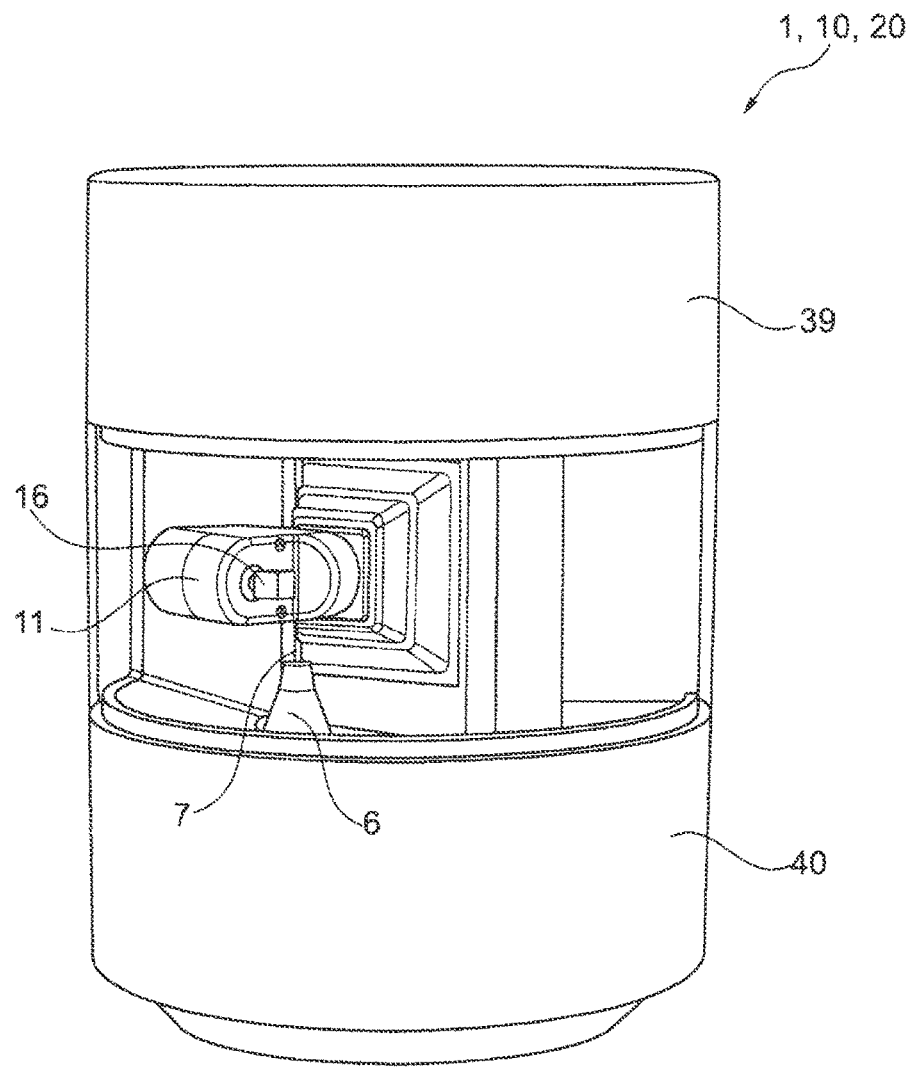
FIG. 6 shows the view of the machining device as a table device

FIG. 6 shows a practical configuration of a machining device 1, 10, 20, as has been illustrated above on the basis of the FIGS. 1 to 5.

The upper area is covered by an upper cover hood 39, while the lower area is covered by a lower cover hood 40.

The central machining area is left blank, and there the workpiece retainer 11 with the workpiece 16 to be machined is visible which is just advanced in the direction of a rotatably driven tool 7 which is clamped in a tool spindle 6.

Figure 7:
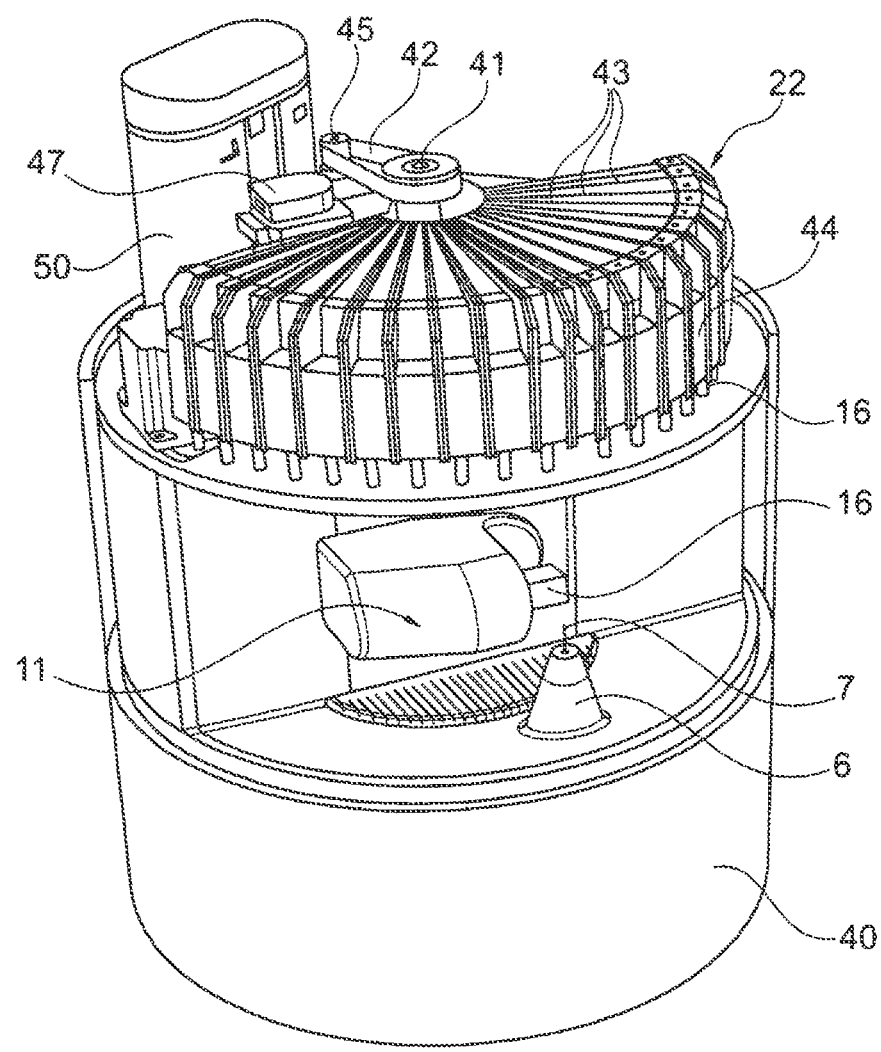
FIG. 7 shows the device of FIG. 6 with a removed upper cover hood

FIG. 7 shows the machining device 1, 10, 20 according to FIG. 6 with a removed upper cover hood 39. There, it is apparent that the workpieces 16 are each received in an allocated plug-in device 44 in the workpiece changer, and that the workpiece changer consists of a number of holding arms 43 wherein each holding arm consists of a horizontal section which vertically bends towards the bottom at its front free end and which comprises the plug-in device 44 at its vertical lower end for receiving the workpiece 16 to be machined.

It is also apparent that the rotary drive of all holding arms, which are connected to one another non-rotatably, is performed by means of a motor whose motor shaft 45 drives the drive shaft 41 of the workpiece changer 22 rotatably by means of a driving belt 42.

Figure 8:
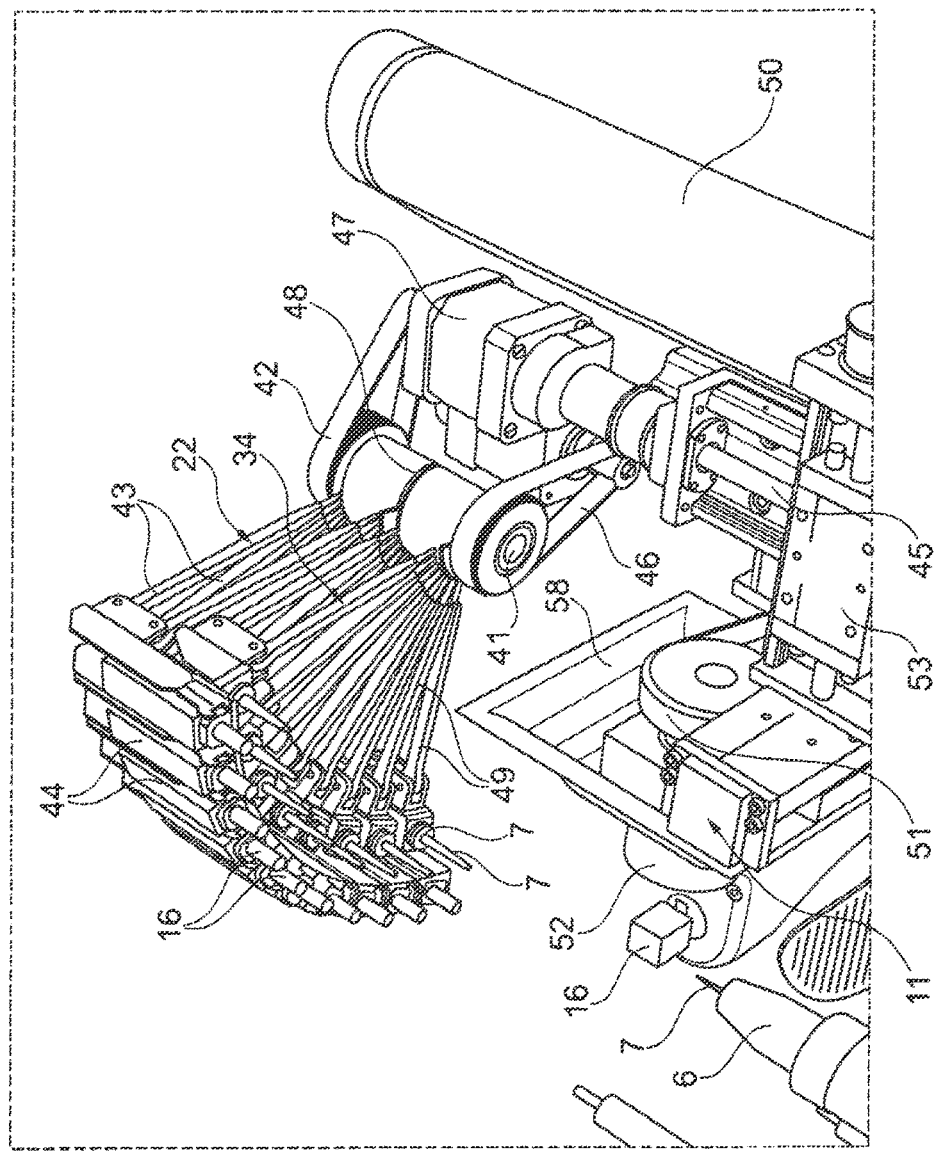
FIG. 8 shows the device of FIG. 7 in a view obliquely from below

Furthermore, a transmission 47 is provided whose function is described in more detail on the basis of FIG. 8.

At the rear part of the machining device 1, 10, 20 a liquid container 50 is apparent.

FIG. 8 shows a perspective bottom view of the arrangement according to FIG. 7 where it is apparent that on an interior and lower plane the tool storage 34 is arranged below the workpiece changer 22 and that, in turn, the tool storage 34 consists of a number of holding arms 49 which are evenly distributed radially on the circumference and which extend towards the outside, wherein at every free end of every holding arm a plug-in device is provided to receive a tool 7 inserted therein.

Accordingly, the holding arms 43 of the workpiece changer 22 are positioned in an upper horizontal plane just above the holding arms 49 of the tool storage 34 arranged below, wherein the tools 7 of the tool storage 34 are positioned on a smaller radius than the workpieces 16 of the workpiece changer 22 which are positioned further to the outside, by way of comparison.

It is also apparent from FIG. 8 that the motor shaft 45 drives the upper driving belt 42 for the workpiece changer 22 by means of a coupling and an associated transmission 47, while the tool storage 34 which is positioned radially on the inside and below the workpiece changer 22 is rotatably driven by means of a further driving belt 46.

Both drives are independent of one another and are separated from one another by a parting gap 48 but are arranged coaxially on the same drive shaft 41.

Parts of the slide drive for the rotational, swivel and traversing movements of the machining device 10 are illustrated schematically.

Two drive shafts which are driven independently of one another are illustrated of which only the driving belts 51 and 52 are identifiable in FIG. 8.

Furthermore, a slide drive 53 is illustrated schematically and it is apparent that the workpiece 16 to be machined is now fed to the fixed spindle 6 with the rotatably driven tool 7 by means of the multi-axis workpiece retainer 11.

Figure 9:
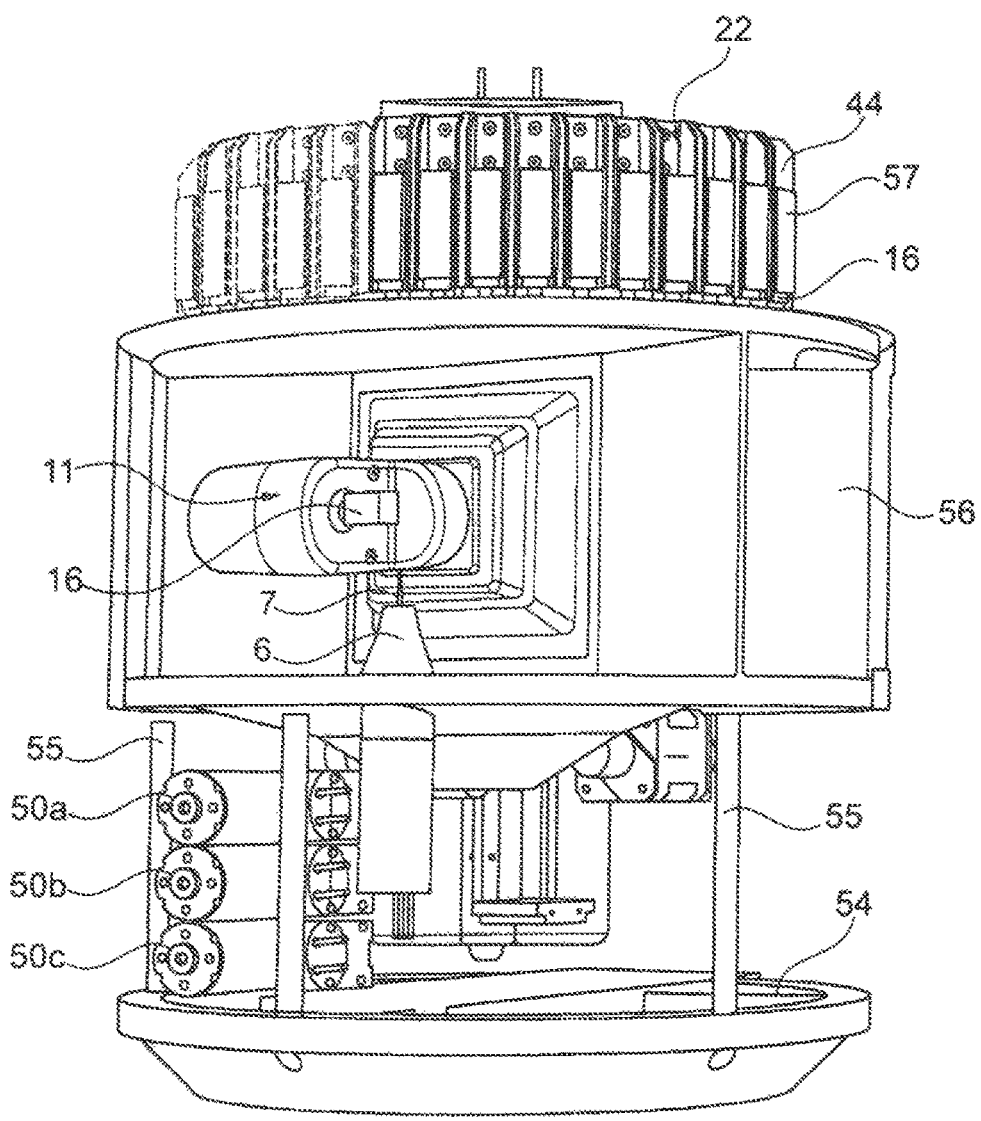
FIG. 9 shows the device of FIGS. 6 to 8 in a side view with removed cover hoods

FIG. 9 shows further details of the device described above wherein only in the side view the parts of the workpiece changer 22 which are positioned radially to the outside are identifiable, and further the plug-in devices associated with the workpiece changer 22 for receiving the workpieces 16.

Further, three planes lying on top of one another are apparent, namely the plane of the upper part 57, the plane of the central part 56 lying below, and the plane of a base plate 54 lying below, on which pillars 55 are arranged which carry the central part 56.

Apart from that, a flexible cover 58 is assigned to the multi-axis workpiece retainer 11, said flexible cover preventing chips from entering the interior of the device during the machining process of a workpiece 16 using the tool 7.

Furthermore, a number of further liquid containers 50*a*, 50*b*, 50*c* are illustrated.

Figure 10:
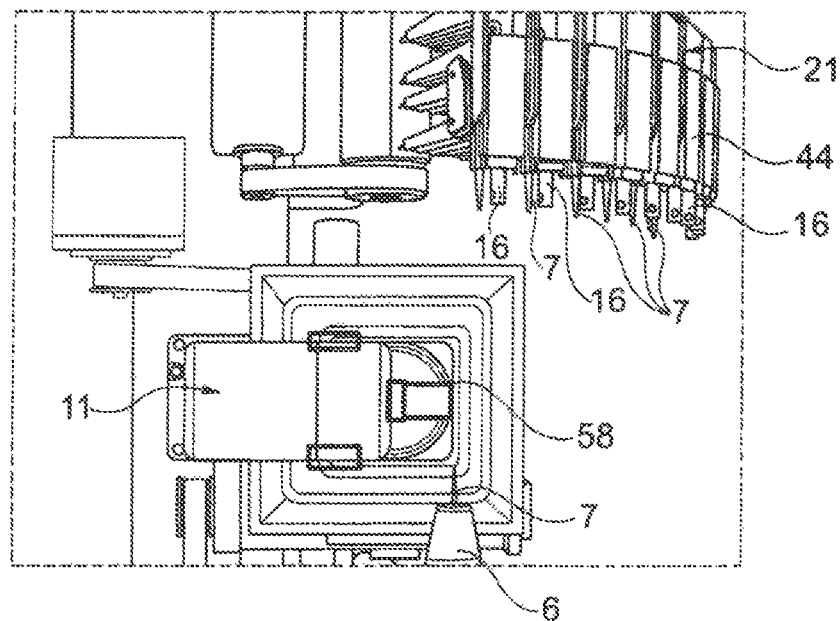
FIG. 10 shows a detailed view of the device of FIG. 9

FIG. 10 shows a detail of the machining device 1, 10, 20 corresponding to the above description, where the same parts are provided with the same reference numerals.

It is apparent that the workpieces 16 to be machined are mounted radially towards the outside in front of the tools 7 of the tool storage 34 which are positioned behind.

Figure 11:
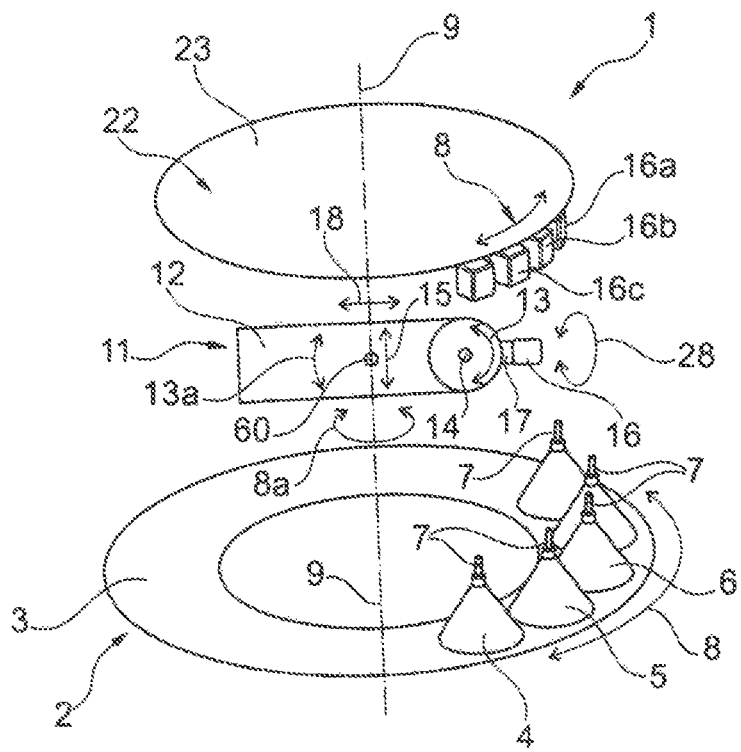
FIG. 11 shows a schematic illustration of an embodiment modified with respect to FIGS. 1 to 5

In FIG. 11 (and in all of the other embodiments) a central vertical axis of rotation 9 is provided, around which a tool retainer 2 is mounted rotatably in the arrow directions 8 which is configured as a rotary table 3 in a preferred embodiment. It is driven by a rotary motor which is not illustrated in more detail.

On the rotary table 3 a number of tool spindles 4, 5, 6 is arranged which are rotatably driven separately, wherein a (possibly) different tool 7 is assigned to every tool spindle 4 to 6. For instance, one tool 7 can be configured as a dental milling cutter, the second tool can be configured as a pin-shaped milling cutter and the third tool can be configured as a grinding wheel and the like.

A workpiece retainer 11 is arranged above the rotary table 3, said workpiece retainer being configured as an X-Y-Z slide 25, 26, 31 in a preferred exemplary embodiment.

In the exemplary embodiment according to FIG. 11 the respective directions of rotation and directions of machining are illustrated. It is apparent that, for instance, a cylinder-shaped base body 12 can be fed in the arrow directions 15 in the vertical direction either to the lower rotary table 3 or to an upper workpiece changer 22. Furthermore, the base body 12 can be driven around a horizontal axis in the direction of tilt 13*a*. In an alternative embodiment it can be provided that the base body 12 is not driven in the direction of tilt 13*a* but that in fact the tool 16 clamped in at the front which is clamped in rotatably in a workpiece holder 17 is driven in the direction of tilt 13 around a swivel axis 14 such that it can be swiveled and tilted. Furthermore, the base body 12 can also be displaceable in the arrow directions 18.

In this way, a displacement in the paper plane of FIG. 11 in the arrow directions 27 is provided such that the workpiece 16 clamped in the workpiece holder 17 is configured to be displaceable and adjustable in any spatial coordinate X, Y, Z.

For machining, the workpiece 16 clamped in the workpiece holder 17 is fed downwards in the arrow direction 15 to the tool retainer 2 and is machined by a correspondingly controlled swivel, rotation and displacement movement as long as the workpiece 16 is machined to completion.

After the machining process has taken place, the workpiece retainer 11 is fed towards the top in the arrow direction 15 towards a workpiece changer 22 which is preferably also configured as a rotary table 23 in a first embodiment. The workpiece changer 22 is driven rotatably around the vertical axis 9 in the arrow directions 8 and comprises a number of workpieces 16a, 16b, 16c at its outer circumference which either have all been machined to completion already or which are picked up from the workpiece retainer 11 as blank workpieces, clamped in the workpiece holder 17 and passed on for machining.

Figure 12:
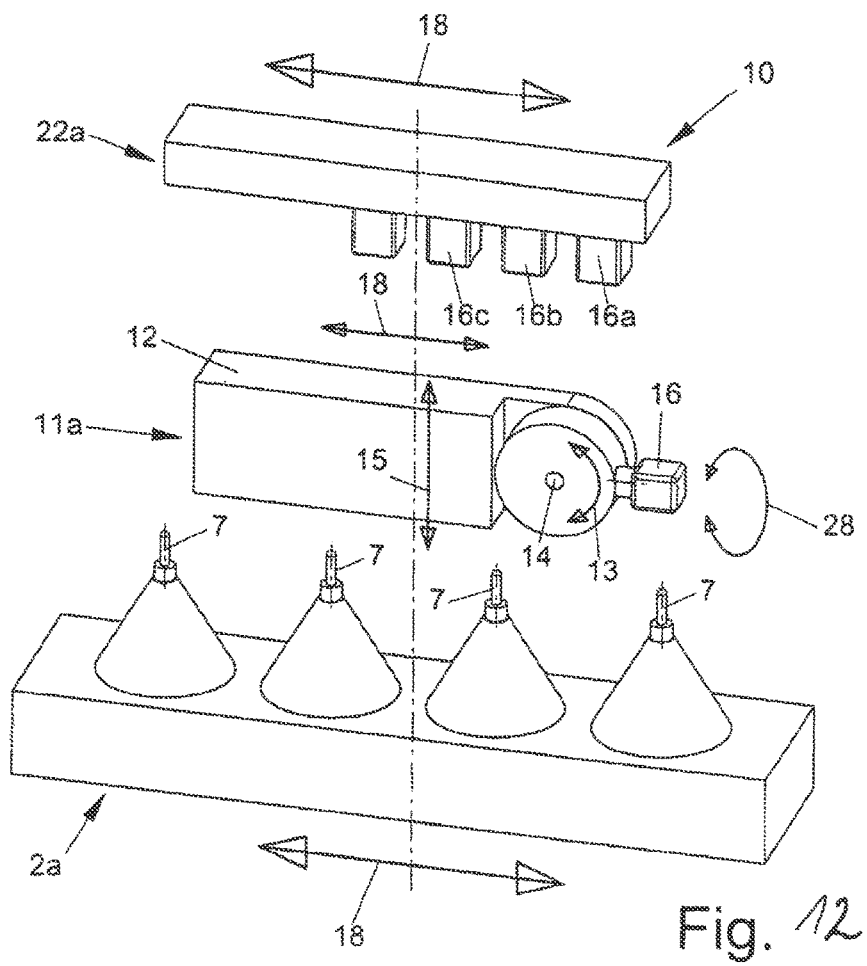
FIG. 12 shows an embodiment modified with respect to FIG. 11

The general basic shape of the machining device 1 according to FIG. 11 can be changed in several ways. FIG. 12 shows another embodiment of a machining device as an exemplary embodiment in which it is apparent that the workpiece changer 22a is configured as a linearly moveable component which can be changed in the arrow directions 18 and which can optionally also be configured to be rotatable in the arrow direction 8—in another embodiment.

Likewise, it is apparent from the exemplary embodiment according to FIG. 12 that the workpiece retainer 11 according to FIG. 11 is configured as a linearly moveable component in its embodiment as a workpiece retainer 11a in FIG. 12, said component being mounted at the vertical axis of rotation 9 such that it can be raised, lowered and swiveled. Thus, it is indicated very generally that the workpiece retainer 11a is configured to be displaceable, rotatable and adjustable in all three spatial axes, without the need for the arrangement of slide elements, such as the slide 25, 26, 31.

FIG. 12 also shows that the configuration of the tool retainer 2 as a rotary table can be omitted and instead a tool retainer 2a can be provided as a linearly displaceable element.

Figure 13:
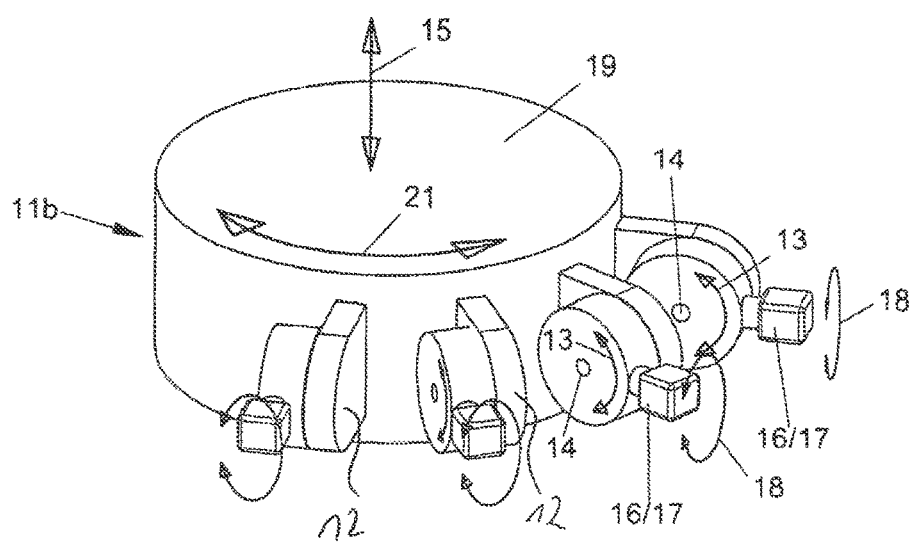
FIG. 13 shows a further embodiment modified with respect to FIG. 11

Complementary to FIGS. 11 and 12, FIG. 13 also shows that the workpiece retainer 11b does not necessarily have to be configured as a three-dimensionally displaceable slide, but it can also consist of a rotary table 19 which is rotatably driven in the arrow directions 21, wherein at its outer circumference a number of different workpiece holders are provided to clamp workpieces 16 to be machined. Thus, as a result, a three-dimensional movement of the workpieces clamped thereat in the individual workpiece holders 17 is achieved, wherein, however, in this embodiment the workpieces can be machined in parallel and optionally also at the same time by the tools 7 in the area of the tool retainer 2.

Figure 14:
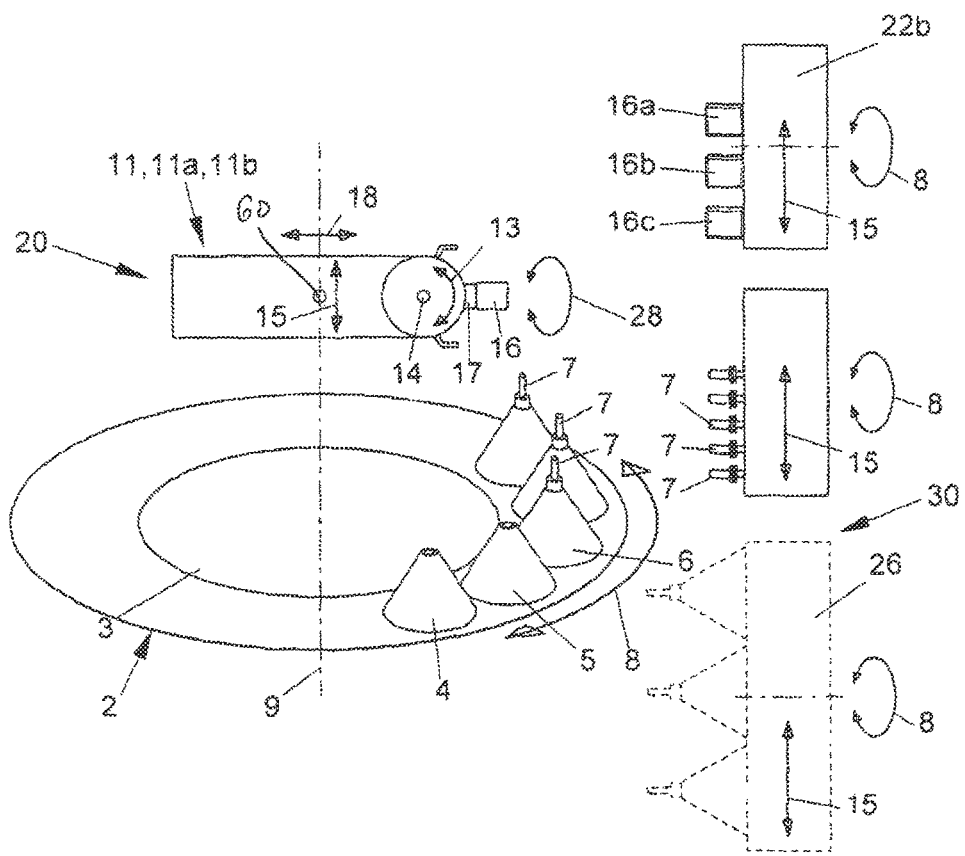
FIG. 14 shows a third embodiment modified with respect to FIG. 11
Figure 15:
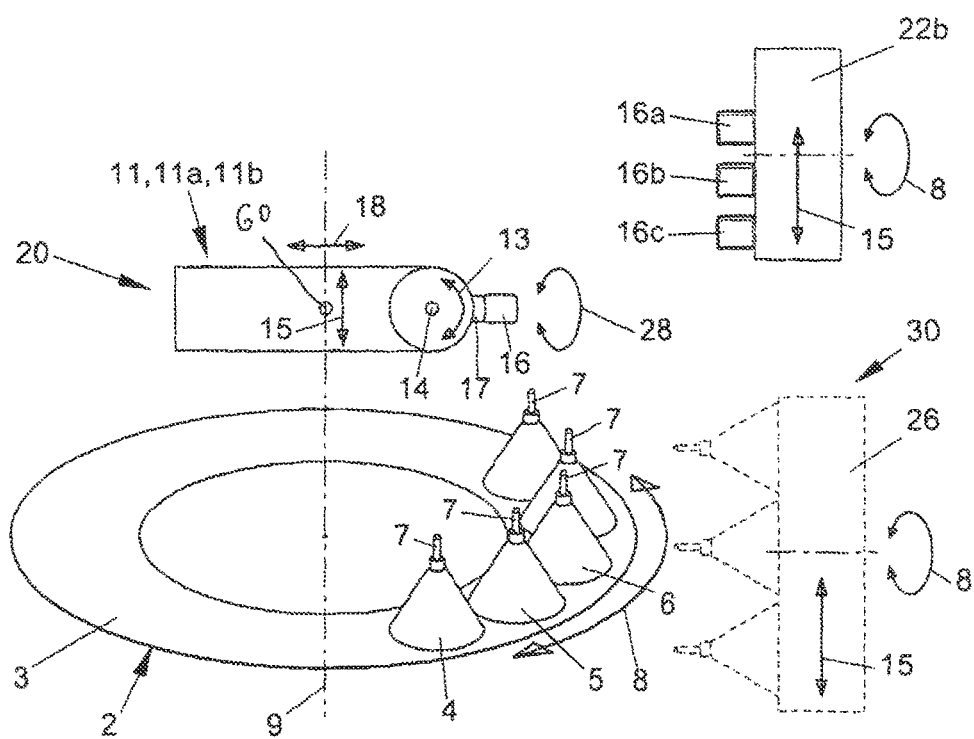
FIG. 15 shows a fourth embodiment modified with respect to FIG. 11
Figure 16:
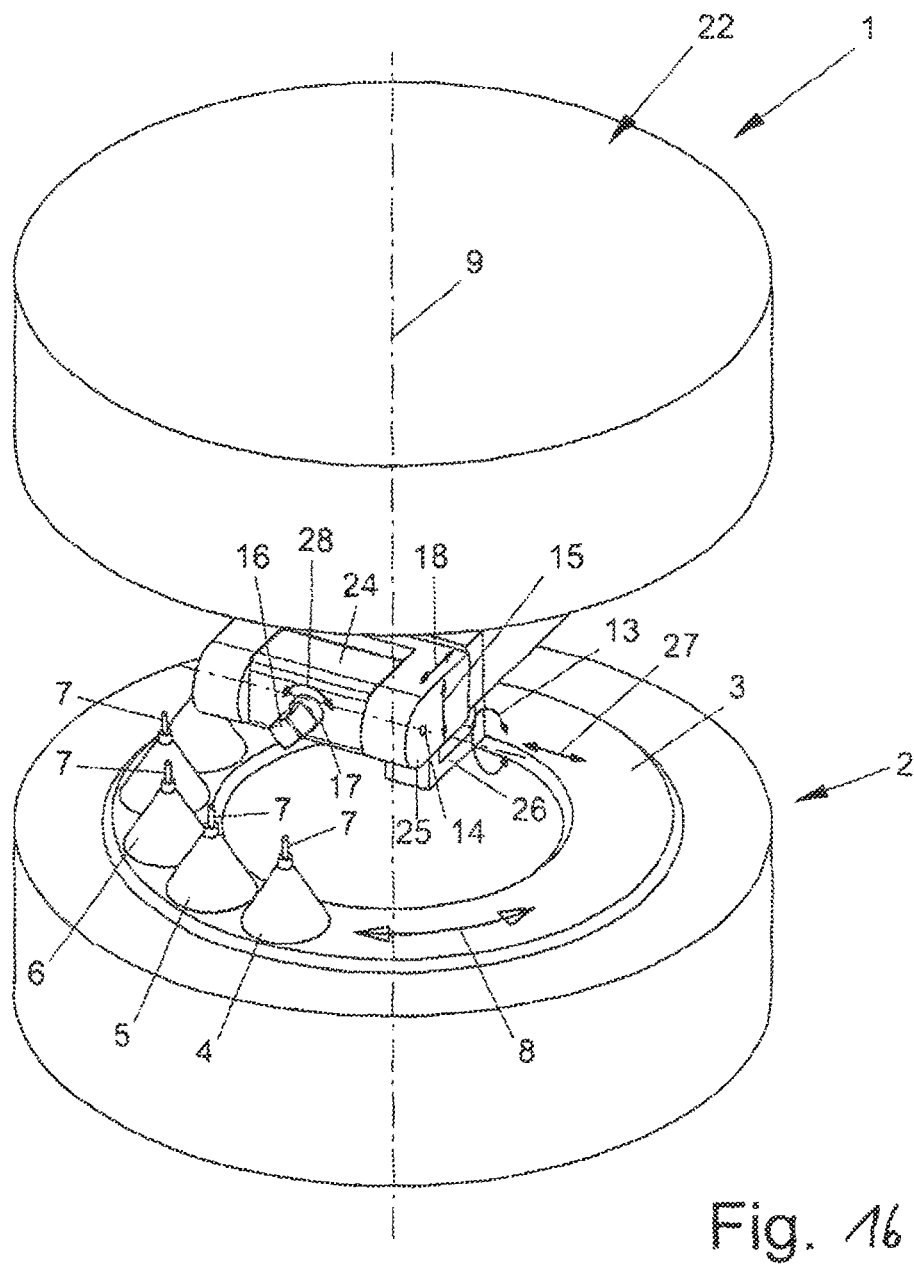
FIG. 16 shows a perspective illustration of a device with a fifth embodiment

FIG. 14 shows a further modification of the embodiments of the FIGS. 11 to 13, wherein every element of the three above-mentioned elements can be exchanged with each other and wherein the combination illustrated in FIG. 14 shall not limit the inventive concept.

It is illustrated that the tool retainer 2 can be replaced with an element 2b which can be moved linearly in the vertical direction such that, instead of a horizontal rotational movement, a vertical displacement movement and optionally also a pertaining rotational movement in the arrow direction 8 takes place.

Thus, what is illustrated in FIG. 14 on the right-hand side in dashed lines is to make clear that the element which is movable linearly and optionally rotatable can also replace the rotary table 3 of the tool retainer 2.

The same applies to the upper workpiece changer 22 which may be configured as a rotary table 23, but which may also be replaced by a linearly moveable element which is configured to be displaceable vertically in the arrow directions 15 and is optionally also configured to be rotatable in the arrow directions 8.

This means that all elements in FIG. 14 can be combined with one another in any desired manner.

Therefore, in FIG. 14 a first type of a machining device 20 is indicated in which the tool retainer 2 is configured as a rotary table 3, the workpiece retainer 11 is configured in its embodiment according to 11a or 11b and the workpiece changer 22b is now configured as a linearly moveable element.

Likewise, FIG. 14 shows on the right-hand side that another type of a machining device 30 can be provided in which the workpiece changer 22b is available, just like the workpiece retainer 11a or 11b or 11, but in which the tool retainer 2b is configured as a linearly moveable element which may optionally also be driven rotatably.

All of the elements which are illustrated graphically in the FIGS. 11 to 14 can form a machining device 1 in any combination with each other.

The FIGS. 15 to 19 show a preferred embodiment of the invention in the manner of a machining device 1 which was illustrated schematically in FIG. 11.

The tool retainer consists of a rotary table 3 which is disposed in a housing shell in a rotatably-driven manner and in which a number of separately driven tool spindles 4, 5, 6 are disposed wherein every tool spindle 4 to 6 is equipped with a different tool 7.

Above the tool retainer 2, the workpiece retainer 11 is disposed which preferably consists of three slides 25, 26, 31 which can be displaced and adjusted relative to one another.

The workpiece 16 to be machined is held by a rotatably driven workpiece holder 17 which is rotatable in the arrow direction 28. The workpiece holder 17 is mounted in a rotary axis 24 rotatably, said rotary axis 24 in turn being configured in the swivel axis 14 in the directions of tilt 13 so as to be swiveled. It forms part of an X slide 25 which performs a displacement of the workpiece 16 in the X coordinate. The X slide 25 is mounted displaceably in a Y slide 26 in order to perform the displacement in the Y direction (arrow direction 27).

Furthermore, the Y slide 26 is mounted displaceably in a Z slide 31 in order to perform a displacement in the arrow direction 15.

Figure 18:
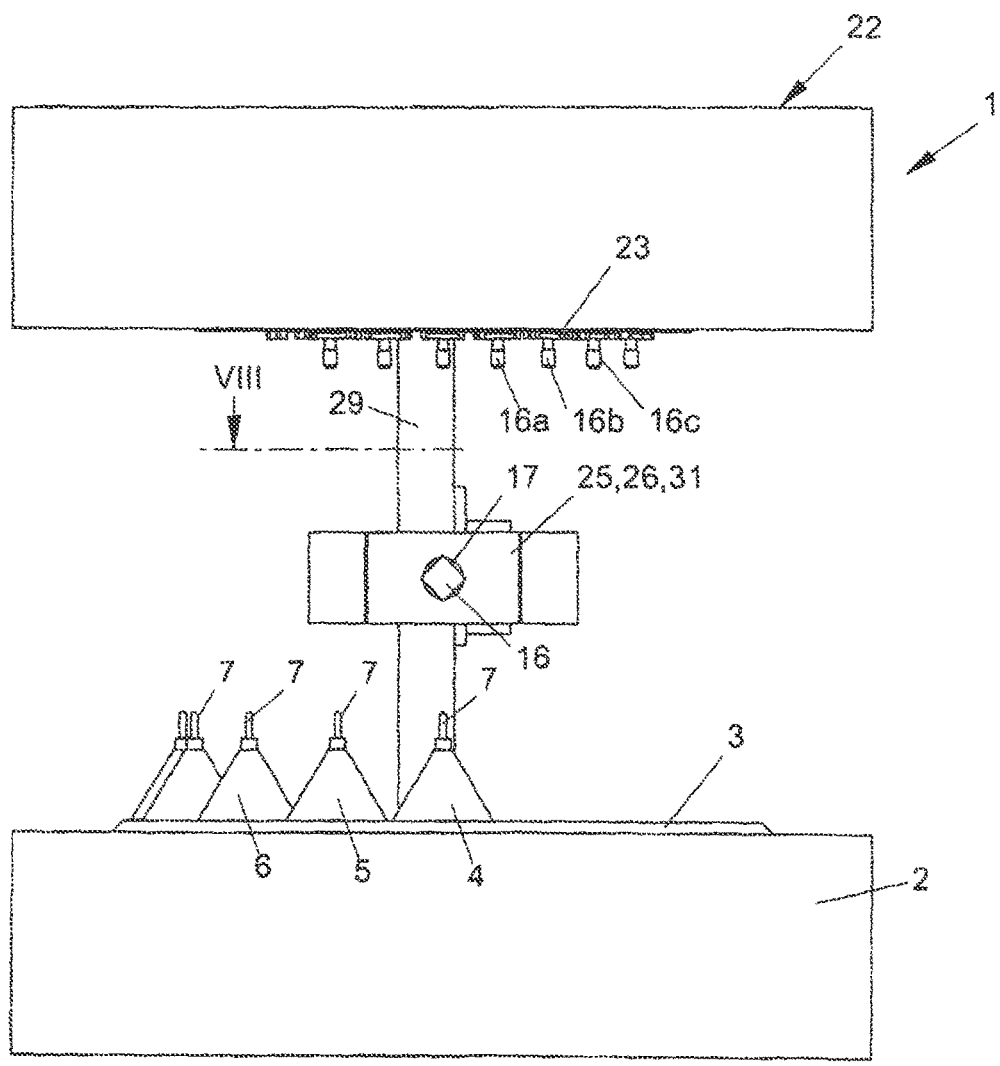
FIG. 18 shows a view which is turned by 90 degrees compared to FIG. 17
Figure 19:
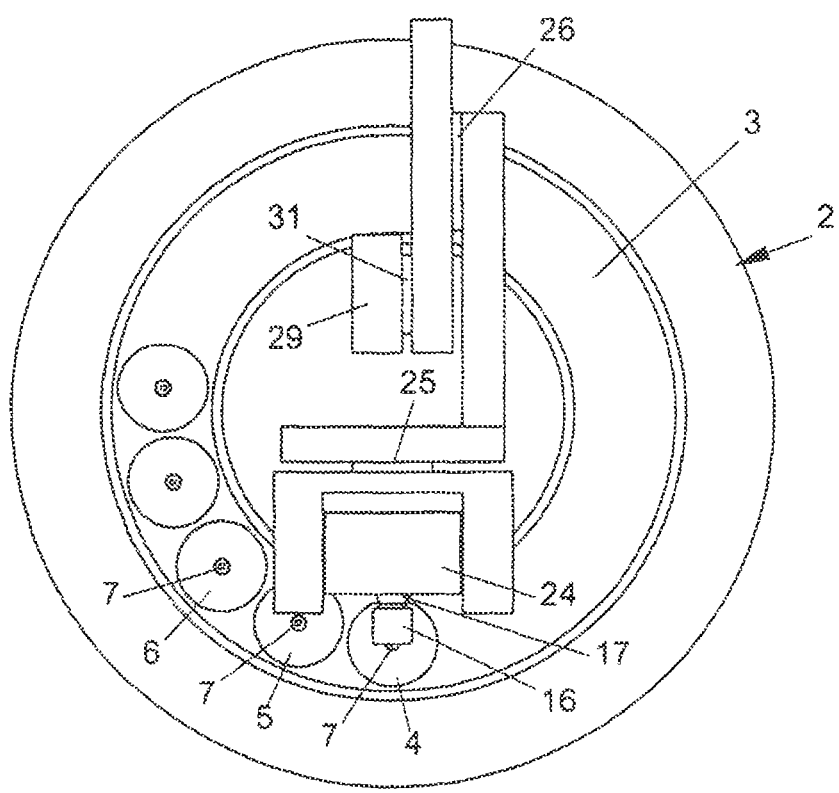
FIG. 19 shows the plan view of the arrangement of FIGS. 16 to 18

The FIGS. 18 and 19 show that the workpiece retainer 11 with its slide elements 25, 26, 31 is disposed in a vertical pillar 29 which forms the connection between the lower tool retainer 2 and the upper workpiece changer 22.

The upper workpiece changer 22 comprises a rotary table 23 at which a number of workpieces 16a, 16b, 16c is disposed so as to be exchangeable.

Here, an easily detachable plug-in device is preferred as a clamping device. Further, the workpiece 16 to be machined is held in a conventional workpiece holder, such as a workpiece clamp, which can be operated mechanically, pneumatically or electromagnetically.

Figure 17:
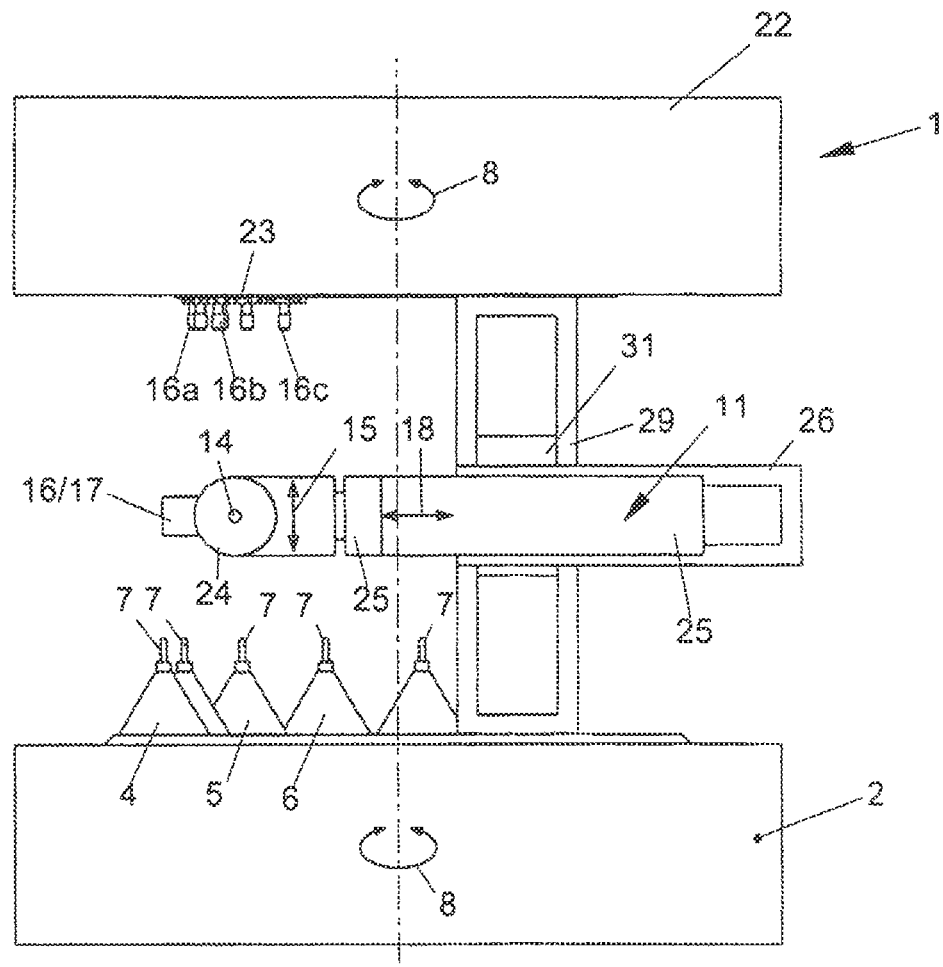
FIG. 17 shows the side view of the embodiment of FIG. 16

The FIGS. 17 and 18 show the slides 25, 26, 31 which can be displaced relative to one another vertically, and thus show the possibility that the workpiece 16 to be machined can be fed to any tool 7 in every desired machining position, swivel position and spatial position and machined thereat.

REFERENCE NUMERAL EXPLANATION 1 machining device
2 tool retainer a,b
3 rotary table
4 tool spindle
5 tool spindle
6 tool spindle
7 tool
8 arrow direction 8*a*
9 axis of rotation
10 machining device
11 workpiece retainer a,b
12 base body
13 direction of tilt 13*a*
14 swivel axis
15 direction of arrow
16 workpiece a, b, c
17 workpiece holder
18 direction of arrow
19 rotary table
20 machining device
21 direction of arrow
22 workpiece changer 22*a, b*
23 rotary table
24 rotary axis
25 X slide
26 Y slide
27 direction of arrow
28 direction of arrow
29 pillar
30 machining device
31 Z slide
32 upper fork
33 lower fork
34 tool storage 34'
35 rotary table
36 direction of arrow
37 direction of arrow
38 position (for 34 in FIG. 2)
39 cover hood
40 cover hood
41 drive shaft
42 driving belt (for 22)
43 holding arm (for 22)
44 plug-in device
45 motor shaft
46 driving belt (for 34)
47 transmission
48 parting gap
49 holding arm (for 34)
50 liquid container
51 driving belt (for 11)
52 driving belt (for 11)
53 slide drive (for 11)
54 base plate
55 pillar
56 central part
57 upper part
58 cover
59
60 rotary and swivel axis (of 11)

The invention claimed is:

1. A machining device for the machine-assisted production and machining of dental workpieces (16), at least one of the workpieces (16) being clamped in at least one workpiece retainer (11) which can be raised, lowered and rotatably driven and which is positioned on a rotational axis (9), and wherein the at least one workpiece retainer feeds the at least one workpiece (16), for the purpose of machining the at least one workpiece while the at least one workpiece (16) is clamped in the at least one workpiece retainer, to at least one tool spindle (4, 5, 6) that is rotationally driven and that has at least one tool (7) secured thereto, wherein the at least one workpiece retainer (11, 11*a*, 11*b*) is configured as a multi-axis robot with at least five degrees of freedom, on one side of the at least one workpiece retainer (11, 11*a*, 11*b*) is arranged at least one tool retainer (2, 2*a*, 2*b*) that is provided with the at least one tool spindle (4, 5, 6) and the at least one tool (7), and wherein on an opposite side of the at least one workpiece retainer (11, 11*a*, 11*b*) are arranged: (i) a tool storage (34), and (ii) a workpiece changer (22, 22*a*, 22*b*) in which the workpieces (16, 16*a*, 16*b*, 16*c*) to be machined are received such that the workpieces can be exchanged between the at least one workpiece retainer (11, 11*a*, 11*b*) and the workpiece chancier (22, 22*a*, 22*b*), wherein the at least one workpiece retainer (11, 11*a*, 11*b*) further comprises (i) a device at a head portion of the at least one workpiece retainer (11, 11*a*, 11*b*), which device is for clamping the workpiece (16) to be machined; and (ii) two gripper forks (32, 33), each gripper fork (32, 33) being configured to receive a respective tool, so as to enable the multi-axis robot to exchange tools between the tool storage (34) and the at least one tool spindle (4, 5, 6).

2. The machining device as claimed in claim 1, wherein the tool storage (34) comprises a plurality of holding arms (49) that together are rotatably driven in the manner of a rotary table (35), and wherein at a respective free end of each of the holding arms (49) a respective tool (7) is received within a respective plug-in device.

3. The machining device as claimed in claim 2, wherein the workpiece changer (22) comprises a plurality of holding arms (43) that together are rotatably driven in a manner of a rotary table (23), and wherein at a respective free end of each of the holding arms of the workpiece changer (43), a respective plug-in device (44) is arranged such that a respective workpiece (16) is held in an exchangeable manner.

4. The machining device as claimed in claim 3, wherein the holding arms (49) of the tool storage (34) are arranged on a common drive shaft (41).

5. The machining device as claimed in claim 1, wherein the at least one workpiece retainer (11, 11*a*, 11*b*) is configured as an X-Y-Z slide such that the clamped workpiece (16, 16*a*, 16*b*, 16*c*) can be moved in all three spatial directions, and can be rotated and swiveled.

6. The machining device as claimed in claim 1, wherein the dental workpieces (16) comprise at least one of artificial teeth or dental replacement parts.

7. A machining device for the machine-assisted production and machining of dental workpieces (16), at least one of the workpieces (16) being clamped in at least one workpiece retainer (11) which can be raised, lowered and rotatably driven and which is positioned on a rotational axis (9), and wherein the at least one workpiece retainer feeds the at least one workpiece (16), for the purpose of machining the at least one workpiece while the at least one workpiece (16) is clamped in the at least one workpiece retainer to at least one tool spindle (4, 5, 6) that is rotationally driven and has a tool (7) secured thereto, wherein the at least one tool spindle (4, 5, 6) comprises a plurality of tool spindles, wherein below the at least one workpiece retainer (11, 11*a*, 11*b*) a tool retainer (2, 2*a*, 2*b*) is arranged that is configured as a rotary table (3), wherein the plurality of tool spindles (4, 5, 6) and their respective tools (7) are placed on the rotary table (3), wherein each of the tool spindles is separately rotatably driven, and wherein arranged above the at least one workpiece retainer (11, 11*a*, 11*b*) is a workpiece changer (22, 22*a*, 22*b*) in which the workpieces (16, 16*a*, 16*b*, 16*c*) to be machined are received, such that the at least one workpiece retainer (11, 11*a*, 11*b*) can exchange workpieces between the at least one workpiece retainer (11, 11*a*, 11*b*) and the workpiece changer (22, 22*a*, 22*b*).

8. The machining device as claimed in claim 7, wherein the at least one workpiece retainer (11, 11*a*, 11*b*) is arranged within an interspace between the tool retainer (2, 2*a*, 2*b*) and the workpiece changer (22, 22*a*, 22*b*).

9. A machining device as claimed in claim 7, wherein the dental workpieces (16) comprise at least one of artificial teeth or dental replacement parts.

* * * * *